United States Patent [19]
Nickel et al.

[11] Patent Number: 5,521,178
[45] Date of Patent: May 28, 1996

[54] COMBINATION MEDICATION CONTAINING FLUPIRTIN AND MORPHINE FOR THE TREATMENT OF PAIN AND THE PREVENTION OF MORPHINE DEPENDENCE

[75] Inventors: Bernd Nickel, Mühltal; Michael Lobisch, Ober-Ramstadt; Istvan Szelenyi, Schwaig; Jürgen Engel, Alzenau; Peter Emig, Niederdorfelden; Gabriela Pergande, Offenbach, all of Germany

[73] Assignee: Asta Medica Aktiengesellschaft, Dresden, Germany

[21] Appl. No.: 141,678

[22] Filed: Oct. 27, 1993

[30] Foreign Application Priority Data

Oct. 30, 1992 [DE] Germany .......................... 42 36 752.2

[51] Int. Cl.⁶ .......................... A61K 31/535; A61K 31/44
[52] U.S. Cl. .......................... 514/231.2; 514/348; 514/349
[58] Field of Search .................................. 514/231.2, 348, 514/349

[56] References Cited

PUBLICATIONS

"Medikamentose Therapie" Fortschr.Med. 110 Jg.(1992) Suppl. 136 pp. 6–12.

"Schmerz und Schmerzbehandlung" by A. Zimmermann Munch.med.Wschr.127(1985)Nr.35 pp. 806–811.

"Allgemeine Pharmakologische Untersuchungen . . ." by Von V. Jakovlev Arzneim.–Forsch/Drug Res. 35(1) Nr. 1 (1985) pp. 44–45; Summary in English attached.

"Untersuchungen zur pharmakologischen Wirkung . . ." by Jakovelv; Arzneim.–Forsch./Drug Res. 35 (1) Nr. 1 (1985) pp. 30–43; Summary in English attached.

*Primary Examiner*—Theodore J. Criares
*Attorney, Agent, or Firm*—Cushman, Darby & Cushman

[57] ABSTRACT

A combination medication containing flupirtin and morphine for the treatment of pain and the prevention of morphine dependence

3 Claims, 6 Drawing Sheets

COMBINATION MEDICATION CONTAINING FLUPIRTIN AND MORPHINE FOR THE TREATMENT OF PAIN AND THE PREVENTION OF MORPHINE DEPENDENCE

The present invention relates to a combination medication for the treatment of pain and the prevention of morphine dependence, and more particularly to a medication containing both morphine and flupirtin in the form of their pharmaceutically acceptable salts.

BACKGROUND OF THE INVENTION

Morphine, which is derived from opium, the dried milky exudate of unripe poppy capsules (Papaver somniferum), has been used in the form of its hydrochloride as an agent against severe pain since its isolation by Serturner (1806). When this analgesic is used frequently and over a long period of time, for example in tumor patients, there is a risk of addiction and the development of tolerance (morphinism).

The side effects observed during correct use, such as euphoric effect, emetic effect, spastic constipation and increase in smooth muscle tone, also reduce the therapeutic effectiveness of morphine.

Therefore, there has been no lack of attempts to synthesize strongly acting, but side effect-free analgesics. Although the partially-synthetic product diamorphine (heroin) is 10 times more effective than morphine, it is more addictive than morphine. Pethidine is about 5 times less effective than morphine and is also less spasmogenic.

Pentazocine and buprenorphine are subject to narcotics legislation because of their potential of causing addiction.

Tramadol is not yet known to present a potential of causing addiction, but it is only about 1/10–1/5 as effective as morphine.

There thus remains a great need for a reliable analgesic medication that is highly effective against severe pain with few side effects and which presents no potential for causing addiction.

It has been proposed to use a combination of active substances to reduce the use of analgesics, or to enhance their inadequate analgesic effect. These attempts have aimed at making the side effects of morphine less pronounced and enhancing its analgesic effect by combining it with selected analgesics.

For example, since morphine has no anti-inflammatory effect, this deficiency in the effectiveness of morphine can be overcome by combining it with anti-inflammatory or anti-pyretic analgesics. Thus, for instance, Vergoni et al. (Life Sci., 50(16), page 135–138 (1992)) describe the potentiating effects of pinacidil on the analgesic effect of morphine. A combination of rectally administered indomethacin with intravenously administered morphine is described by Segstro and Morley-Forster in Can. J. Anaesth. 38(5), 578–581 (1991).

Animal experiments which describe the potentiation of analgesic effects of morphine and clonidine in rats were reported by Wilcox, Carlsson, Jochim and Jurna in Brain Res. 405(1), 84–93 (1987).

All experiments are aimed at enhancing the analgesic effects in the sense of a synergistic effect in order to reduce the dose of analgesic or anti-inflammatory agent and morphine.

Flupirtin (INN) is an analgesic with muscle-relaxing components of action. (B. Nickel, V. Jakovlev, I. Szelenyi, Arzneim.—Forsch. 40(II)8, 909–911 (1990) German published patent 36 01 195).

It has no dependence potential (B. Nickel, H. O. Barbe, I. Szelenyi, Arzneim.—Forsch. 40(II)8, 905–908 (1990)). The antinociceptive effect of flupirtin cannot be antagonized by naloxon. Flupirtin also shows no affinity for opiate receptors. (B. Nickel, A. Herz, V. Jakovlev, U. Tibes, Arzneim.—Forsch. 35(II), 1402 (1985)).

SUMMARY OF THE INVENTION

In accordance with the present invention, it has now been found that flupirtin, given alone, does not lead to the development of tolerance. It was also surprisingly found that there were no signs of tolerance when the combination of flupirtin and morphine was administered. This is unexpected since the structure of flupirtin differs greatly from the known morphine antagonists naloxon or methadone.

Therefore, it is an object of the present invention to provide improved medications which have an analgesic action and which display a greatly reduced addiction potential or even no addiction potential at all.

These and other objects are achieved by a medication consisting essentially of flupirtin or a pharmaceutically acceptable salt thereof in the amount of 10 mg to 1000 mg calculated as flupitin base and a pharmaceutically acceptable salt of morphine in the amount of 5 mg to 500 mg, calculated as flupirtin base. (The weights set out herein always relate to the free bases, unless otherwise indicated.) Of course, the two medications can be combined into a single dosage unit or they may be administered concurrently.

Administration of flupirtin over several weeks did not lead to tolerance in animal experiments. (FIG. 1). The analgesic effect was maintained over the entire duration of the experiment (45 days).

The examination was conducted in the electro-pain test in the rat (after Blake et al. Arz. Med. exp. 4, 146 (1963)). An additive, antinociceptive effect was observed after the single administration of flupirtin in combination with morphine. (FIG. 2).

Administration of flupirtin by itself produces an antinociceptive effect of 45%, whereas the administration of the combination with morphine yields an effect of 100%.

Physical dependence, the often described symptom of dependence due to morphine, can be demonstrated by decrease in animal weight after withdrawal. This effect was significantly reduced by flupirtin in combination with morphine (FIG. 3). That is, flupirtin eliminates or weakens the physical dependence potential of morphine.

It may also be assumed that flupirtin eliminates or markedly diminishes the dependence and withdrawal symptoms provoked by other combinations such as those of the barbiturate, alcohol, amphetamine, cocaine, cannabis or hallucinogen type.

The test for the possible presence of psychological or mental dependence was conducted according to the method of Hosoya, Pharmacol. Meth. Tox, 5, 515 (1979).

The behavior of animals on the day of withdrawal was recorded during the same long-term investigation. It was also found in this model that the behavior of the animals was markedly influenced by flupirtin in the combination after withdrawal of morphine (stimulation, rearing) (FIGS. 4 and 5). The marked stimulation or reproductive behavior of the animals after morphine is reduced in the combination with flupirtin and rather resembles that of untreated control animals. Flupirtin also relieved the rigidity provoked in animals by morphine. (FIG. 6).

The combination of active ingredients can be formulated as follows: Each tablet or other dosage unit of the medication contains for example 10 mg to 1000 mg flupirtin in the form of a pharmaceutically acceptable salt and 5 mg to 500 mg morphine in the form of a pharmaceutically acceptable salt. Preferably each tablet or other dosage unit contains 50 mg–500 mg flupirtin and 10 mg–250 mg morphine.

Salt formers that may be considered in the case of flupirtin are for example hydrochloric acid, gluconic acid, malonic acid and maleic acid; in the case of morphine, mineral acids such as hydrochloric acid and sulfuric acid may be considered.

The medication of the invention may be supplied in the form of tablets, capsules, pellets, granulates, ampoules for intravenous and intramuscular injection, in the form of infusion solutions and suppositories. The preparation of the medication is carried out in known manner, using known and conventional pharmaceutical auxiliary substances as well as other conventional carriers and diluents being used.

Carriers and auxiliary substances of this kind that may be used are for example substances recommended or listed in the following literature references as auxiliary substances for pharmaceutical, cosmetic and adjacent fields: Ullmanns Encyklopädie der technischen Chemie, Volume 4 (1953), page 1 to 39; Journal of Pharmaceutical Sciences, Volume 52 (1963), page 918 et seq.; H.v. Czetsch-Lindenwald, Hilfsstoffe für Pharmazie und angrenzende Gebiete; Pharm. Ind. Issue 2, 1961, page 72 et seq.; Dr. H. P. Fiedler, Lexikon der Hilfsstoffe für Pharmazie, Kosmetik und angrenzende Gebiete, 2nd edition, Editio Cantor, Aulendorf in Wurttemberg 1981 and Pharmazeutische Technologie (publishers: Fuchs, Sucker, Speiser, Georg Thieme Verlag, 2nd edition (1991).

BRIEF DESCRIPTION OF FIGURES OF DRAWING

Figure 1:
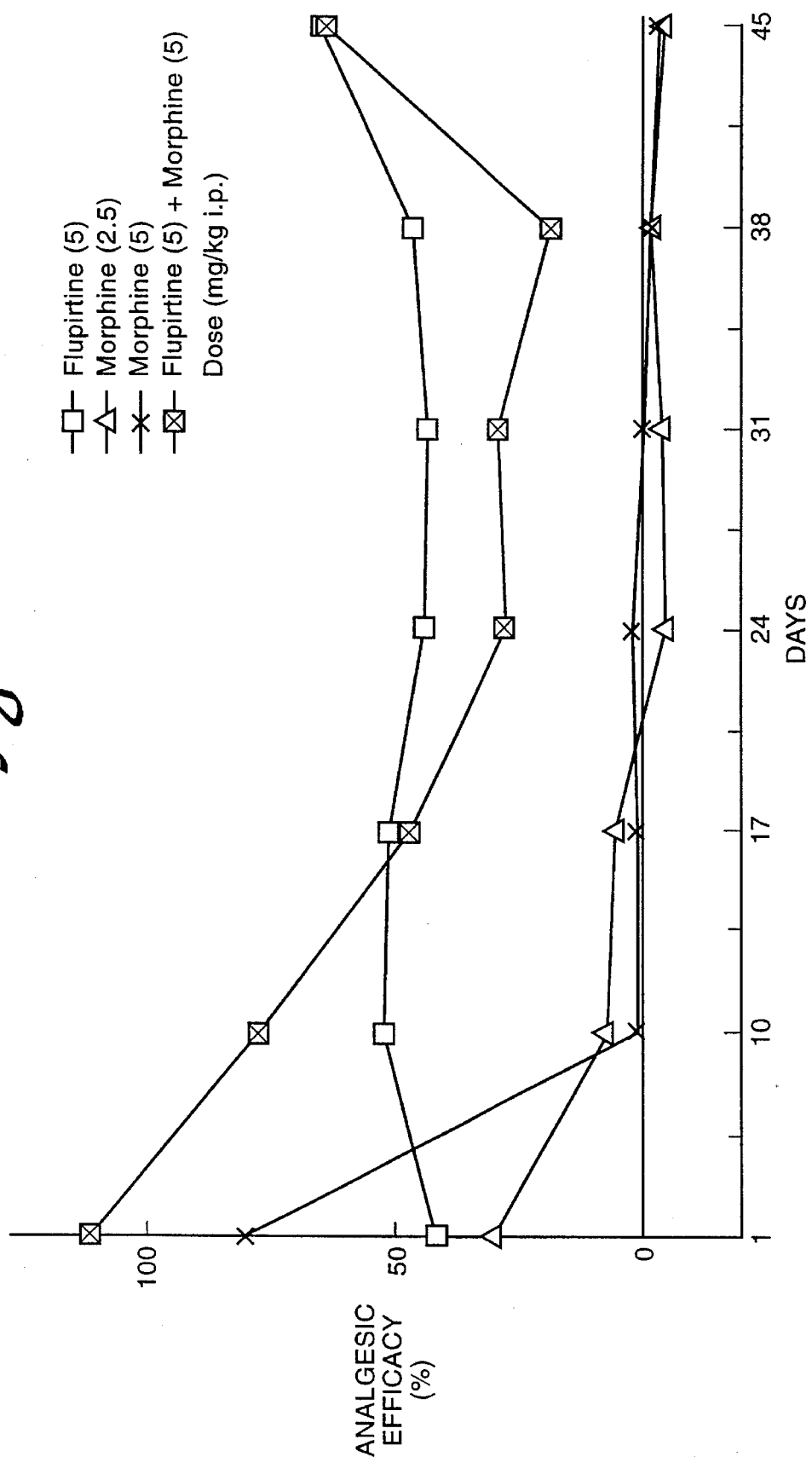
FIG. 1 illustrates the development of tolerance over 45 days of the combination compared to the individual substances.
Figure 2:
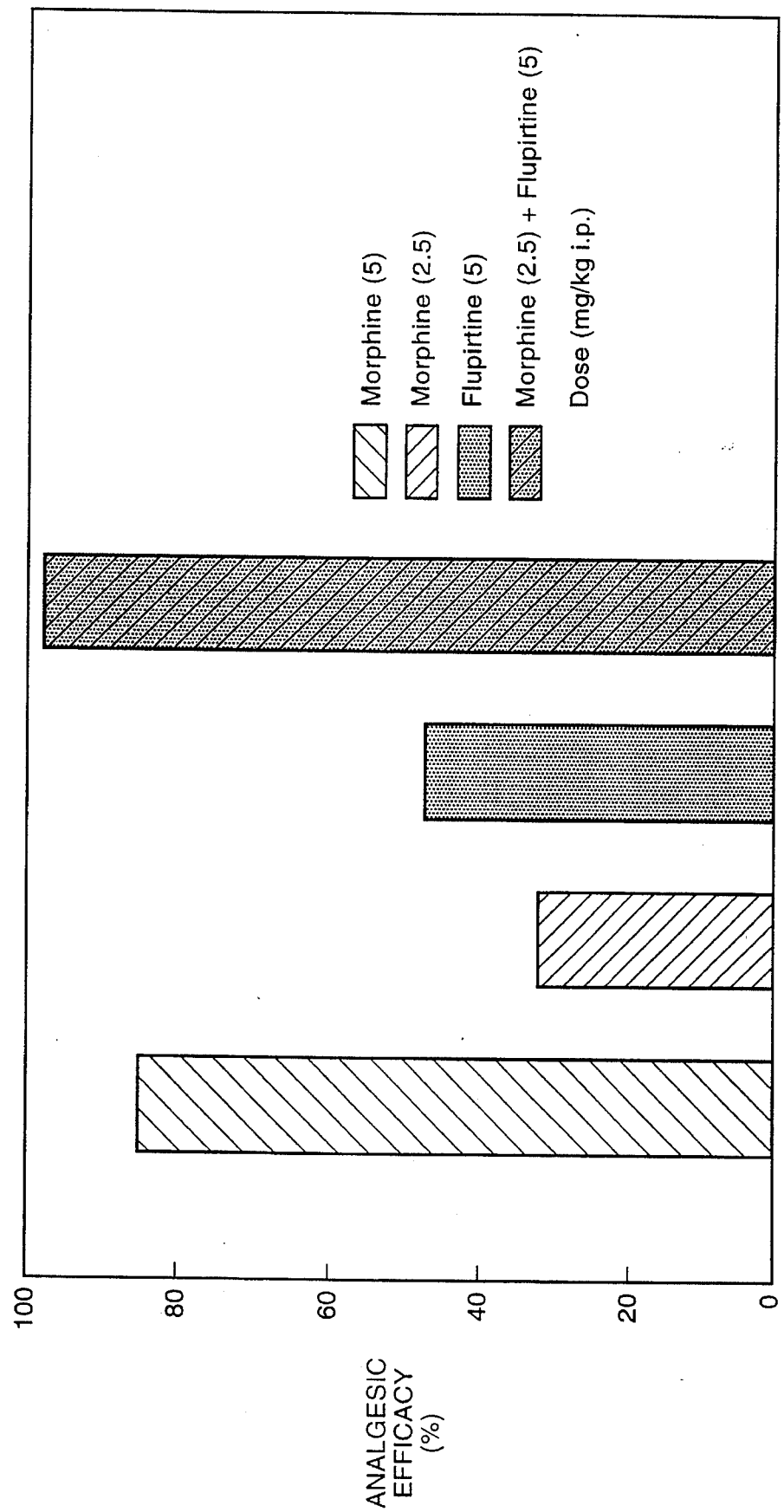
FIG. 2 shows the antinociceptive effect of the combination compared to the individual substances.
Figure 3:
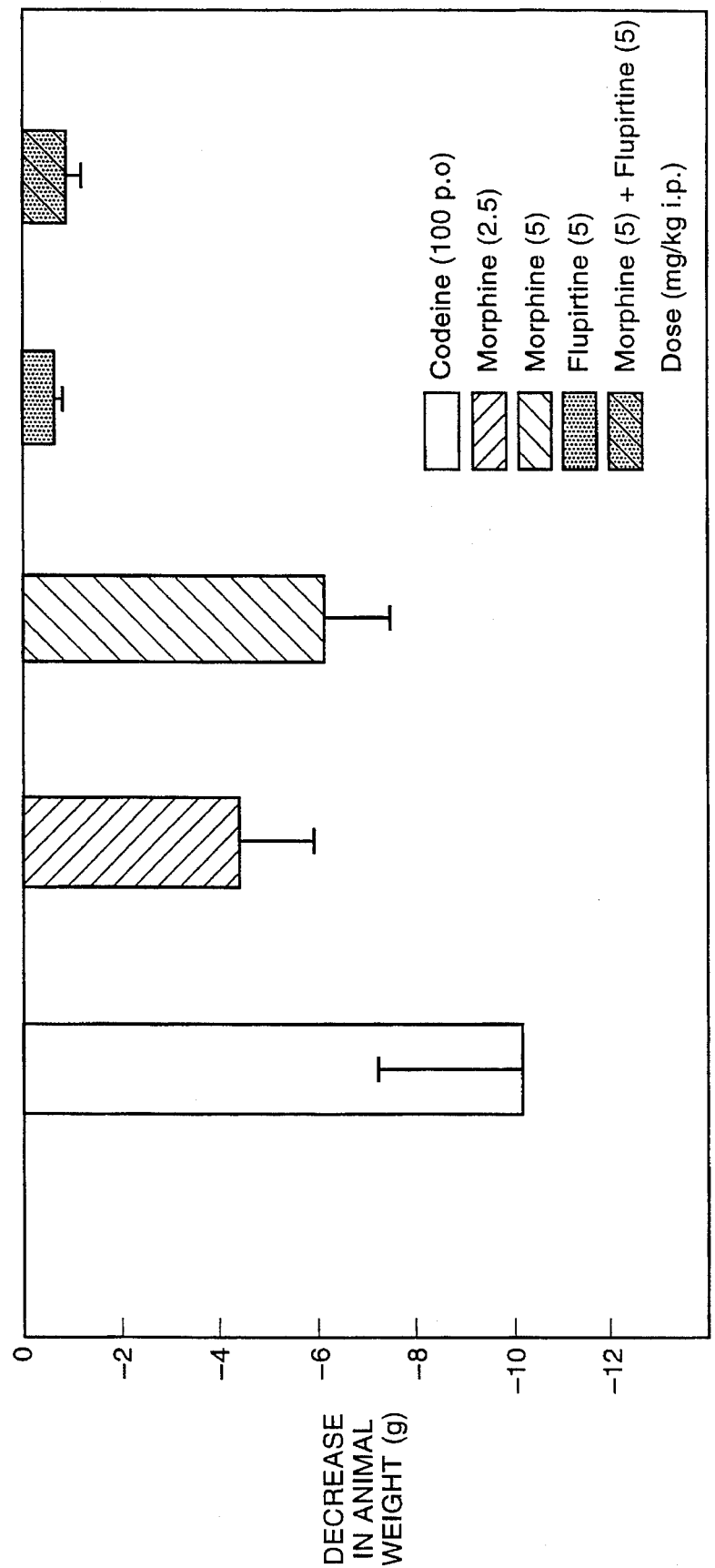
FIG. 3 shows the results of a trial on mental dependence.
Figure 4:
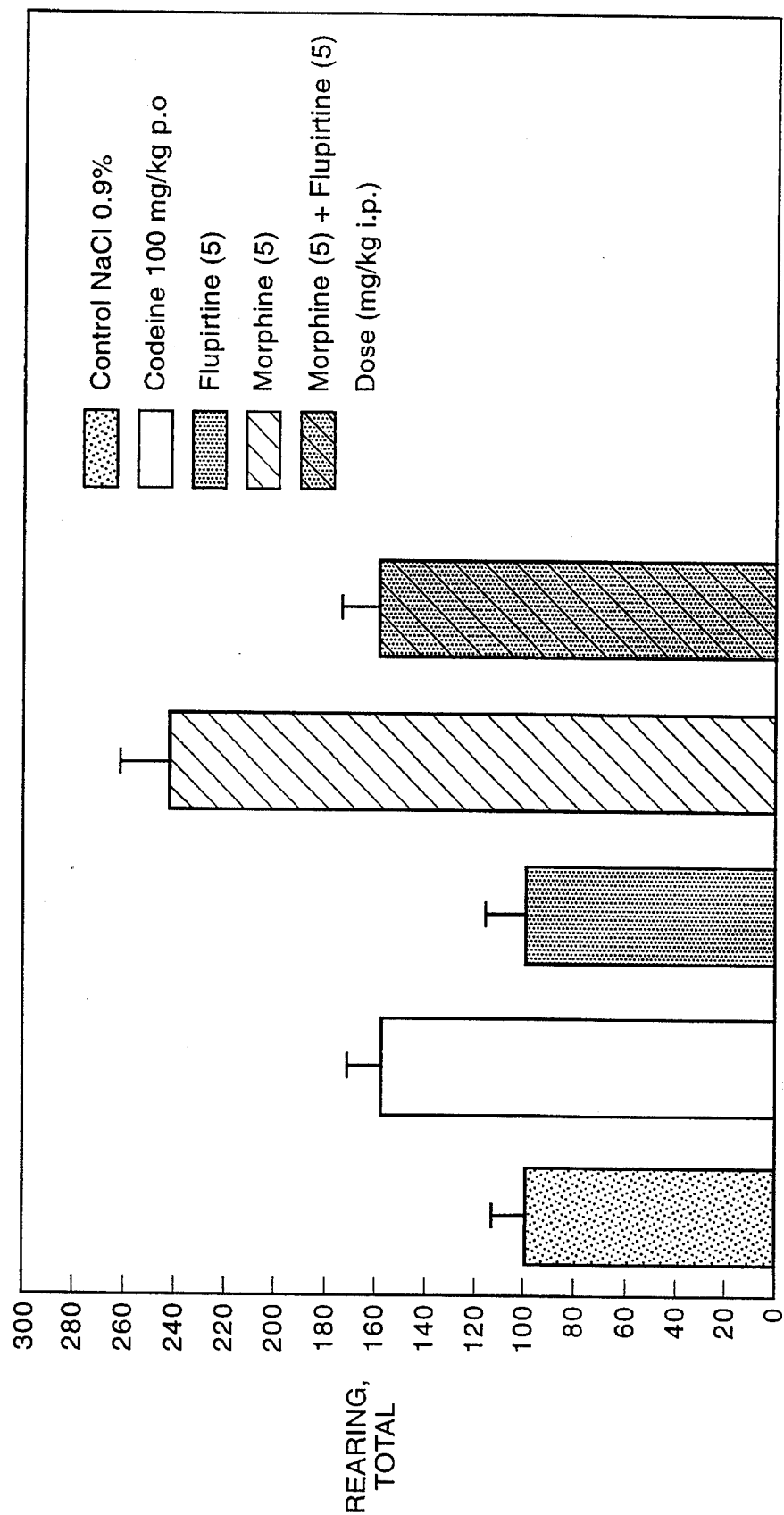
FIG. 4 shows on the basis of the rearing of rats the stimulatory effect of morphine alone and the non-stimulatory effect of the combination of the invention.
Figure 5:
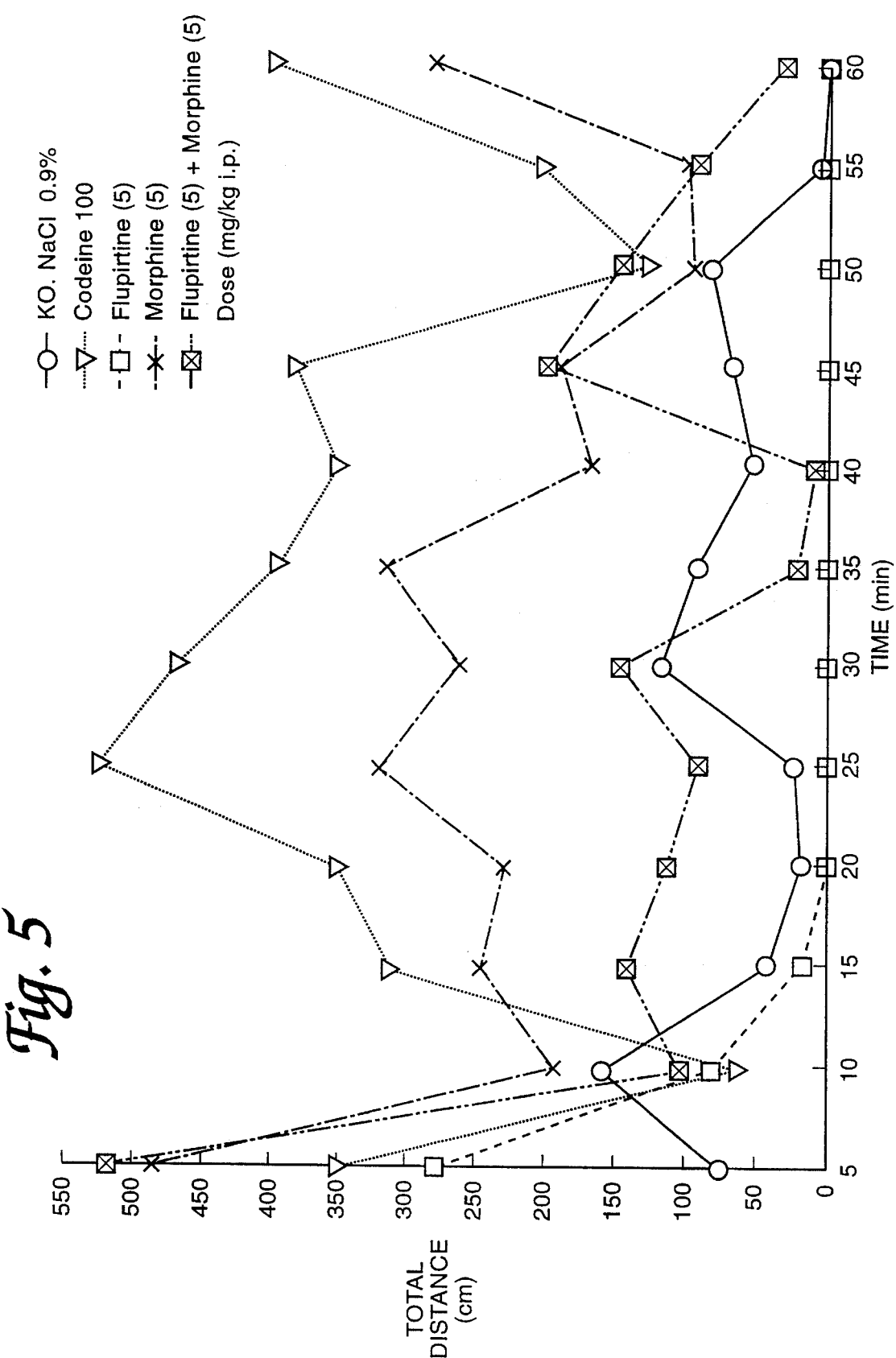
FIG. 5 shows a similar version as FIG. 4: here the path is measured as an indication of the stimulation of the animals.
Figure 6:
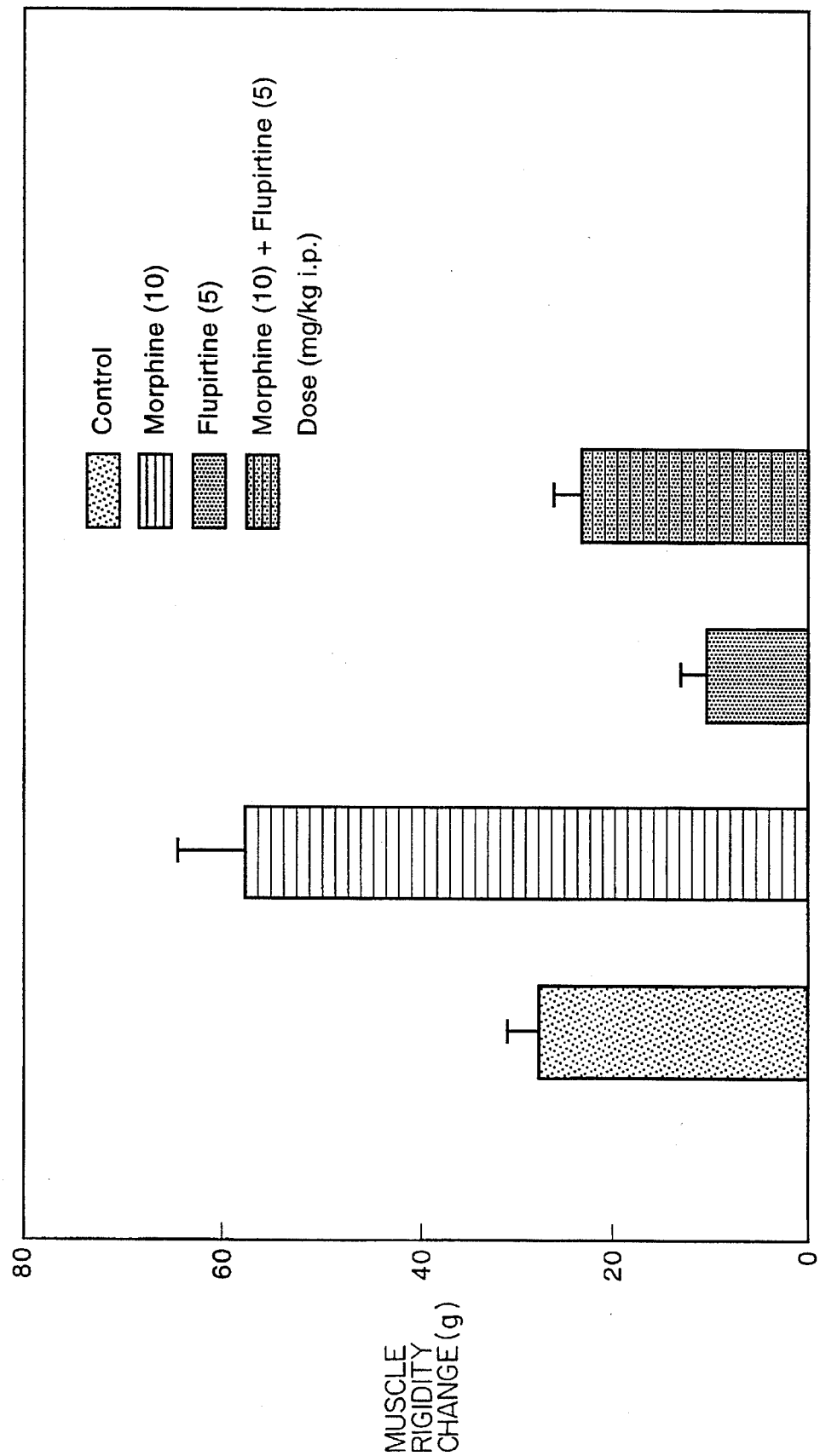
FIG. 6 shows the influence of the individual substances on muscle relaxation compared to the combination of the invention.

What is claimed is:

1. A pharmaceutical dosage unit consisting essentially of flupirtin or a pharmaceutically acceptable salt thereof in an amount of 5 mg/kg calculated as the base and a pharmaceutically acceptable salt of morphine in an amount of 2.5 mg/kg to 10 mg/kg, calculated as the base, wherein said pharmaceutical dosage unit is capable of preserving the analgesic effectiveness of the morphine and removing potential for developing drug dependence and tolerance development on the morphine in a patient to whom the pharmaceutical dosage unit is administered.

2. A method of providing an analgesic effect in a patient in need thereof which comprises administering an effective amount of the pharmaceutical dosage unit set forth in claim 1.

3. A method of providing an analgesic effect in a patient in need thereof which comprises concurrently administering 5 mg/kg of flupirtin or a pharmaceutically acceptable salt thereof and 2.5 mg/kg to 10 mg/kg of a pharmaceutically acceptable salt of morphine, wherein the analgesic effectiveness of the morphine is preserved and potential for developing chemical dependence on the morphine is reduced in the patient.

* * * * *